United States Patent [19]

Heyes et al.

[11] 3,956,262
[45] May 11, 1976

[54] TRIAZENOIMIDAZOLES
[75] Inventors: James Heyes, Peaslake; Neal Ward, Walton-on-the Hill, both of England
[73] Assignee: Beecham Group Limited, United Kingdom
[22] Filed: Nov. 27, 1974
[21] Appl. No.: 527,655

Related U.S. Application Data
[63] Continuation of Ser. No. 205,345, Dec. 6, 1971, abandoned.

[30] Foreign Application Priority Data
Dec. 9, 1970 United Kingdom............... 58385/70

[52] U.S. Cl............................... 260/140 R; 260/141; 260/309.6; 260/465.5 R; 260/566 R; 424/226
[51] Int. Cl.$^2$.................. A01N 9/20; A61K 31/655; A61L 9/00; C07C 107/00
[58] Field of Search..................................... 260/140

[56] References Cited
UNITED STATES PATENTS
3,649,613  3/1972  Krauth et al....................... 260/140

OTHER PUBLICATIONS
Shealy et al. (I), J. Org. Chem., Vol. 27, pp. 2150–2154, (1962).
Shealy et al. (II), J. Med. Chem., Vol. 9, pp. 34 to 38, (1966).
Shealy et al. (III), J. Pharm. Sciences, Vol. 56, pp. 147–148, (1967).
Shealy et al. (IV), Nature, Vol. 210, p. 208, (1966).

*Primary Examiner*—Floyd D. Higel

[57] ABSTRACT
Imidazolyl derivatives of the formula

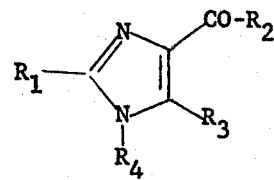

or a tautomer or structural isomer thereof, wherein
  $R_1$ is a carbocyclic or heterocyclic aromatic group unsubstituted or substituted by one or more halogen, unsubstituted or substituted hydroxyl, amino, thiol, sulphonic or carbocyclic groups, cyano, nitro, acyl, alkyl, aryl or haloalkyl;
  $R_2$ is amino or hydroxyl, or alkoxyl, aryloxyl or aralkoxyl unsubstituted or substituted by one or more halogen, or unsubstituted or substituted hydroxyl or tertiary amino;
  $R_4$ is a negative charge when $R_3$ is $N_2^+$ of $R_4$ is hydrogen or $C_{1-6}$ alkyl when $R_3$ is $N=NR_5R_6$, wherein $R_5$ is methyl or halogen $\beta$-substituted ethyl and $R_6$ is hydrogen, a hydrocarbon unsubstituted or substituted by halogen, or an unsubstituted or substituted hydroxyl or tertiary amino; or an acid addition salt, solvate or solvated acid addition salt thereof;

are useful for their bacteriocidal and antifungal activity and for their antitumor activity against R1 lymphoma, ADJ/PC6 plasma cell tumor and Friend Leukaemia in mice.

The imidazole derivatives, wherein $R_3$ is $N_2^+$ and $R_4$ is a negative charge, are intermediates particularly useful in the production of the final product imidazoles having the above specified utilities.

5 Claims, No Drawings

TRIAZENOIMIDAZOLES

This is a continuation of application Ser. No. 205,345 filed Dec. 6, 1971, now abandoned.

The present invention relates to novel substituted imidazoles, having pharmacodynamic activity, to processes for their preparation and to pharmaceutical compositions containing them.

Since the initial communication of the anti-tumour activity of 5-(3,3-dimethyl triazeno) imidazole-4-carboxamide (Ia) (D.I.C.) and some analogues in 1962 [Shealy et.al., Biochem. Pharmacol, 11, 674 (1962) and J. Org. Chem., 27, 2150 (1962] it has been mentioned in many papers that these agents are analogues of 5-amino-imidazole-4-carboxamide (Ib) (A.I.C.) which is an imidazole present in the biosynthetic pathway to purine ribonucleotides and nucleic acids.

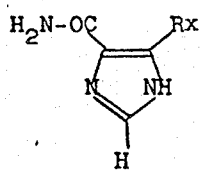

(Ia) $R^x = NNN(CH_3)_2$ (Ib) $R^x = NH_2$

Since 1962 almost all modifications of D.I.C. and A.I.C. made by those interested in anti-tumour activity have kept a close as possible to the structure (I), that is, they have generally kept the group (II)

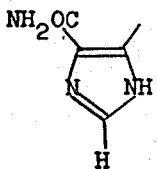

as it was apparently widely accepted as essential for the retention of activity.

Canadian Pat. No. 871,699 has disclosed triazenoimidazoles of general formula (III)

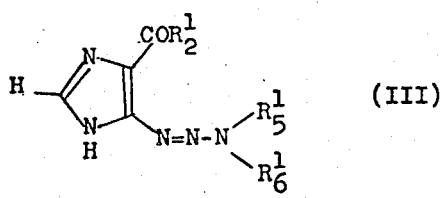

wherein $R_2{}^1$ is an amino or optionally substituted hydroxyl group and $R_6{}^1$ and $R_5{}^1$ are optionally substituted hydrocarbon groups. These compounds are stated to have some anti-luekemia and anti-biotic activity but it is suggested that their use be limited to sanitizing bed linen.

One particularly successful modification of the A.I.C. structure is 5-[3,3-Bis(2-chloroethyl)-1-triazene] imidazole-4-carboxamide (IV)

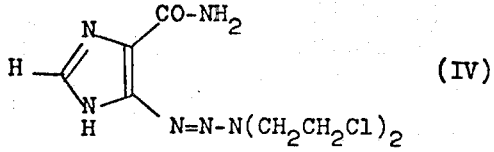

which has been described by Shealy et.al. (Journal of Pharmaceutical Sciences, 57, 83–86 (1968) as an unstable compound that isomerises rapidly. While the compound (IV) was reported to have some activity in the mouse lymphoid leukemia L1210 test system of Shealy et.al. (Nature, 210, 208 (1966)) it was also stated that the isomerisation product that formed unless (IV) was kept in the absence of light at sub zero temperatures was not active against leukemia. Furthermore, compound (IV) was reported to be difficult to prepare and also it required the prior formation of 5-diazoimidazole-4-carboxamide (V)

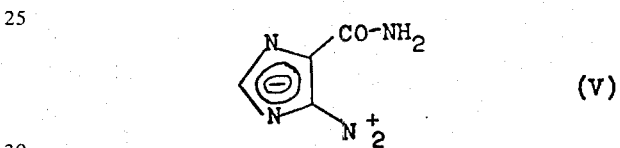

which is also unstable.

The preparation of compounds of formulae (III) and (IV) is consistant with the fact that no modifications in the 2-position have been reported or even suggested. This again is thought to be due to the above mentioned commonly held belief that modifications should resemble as closely as possible the naturally occurring purine precursor A.I.A.

Surprisingly, we have now found that a fundamental change may be made in the group (II) that leads to compounds of increased stability and retained biological activity coupled in some cases with decreased toxicity.

Accordingly, the present invention provides compounds of general formula (VI)

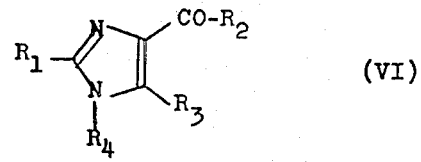

or a tautomer or structural isomer thereof as hereinafter defined wherein $R_1$ is a carbocyclic or heterocyclic aromatic group, optionally substituted by one or more halogen atoms, optionally substituted hydroxyl, amino, thiol, sulphonic or carboxylic groups, cyano, nitro, acyl, alkyl, aryl or haloalkyl groups; $R_2$ is an amino or hydroxyl group or an alkoxyl, aryloxy or aralkoxyl group optionally substituted by one or two halogen atoms or optionally substituted hydroxyl or tertiary amino groups; $R_4$ is a methyl group or negative charge when $R_3$ is $N_2{}^+$ or $R_4$ is H or a methyl group when $R_3$ is a group $N=N—NR_5R_6$ wherein $R_5$ is a methyl or β-halogen-substituted ethyl group and $R_6$ is a hydrogen or a hydrocarbon group optionally substituted by a halogen atom or an optionally substituted hydroxyl or tertiary amino group; and salts, solvates or solvated salts thereof.

Preferably $R_4$ is a hydrogen atom. Suitable groups $R_1$ include phenyl or naphthyl groups or 5- or 6-membered heterocyclic groups such as the pyridyl, furyl, thiazolyl, thienyl, oxazolyl and like groups any of which may be substituted by one or more fluorine, chlorine, bromine or iodine atoms, hydroxyl, methoxyl, benzyloxyl, nitro, methyl or like groups.

Preferred groups $R_1$ include the phenyl, naphthyl, tolyl, fluorophenyl, chlorophenyl, dichlorophenyl, nitrophenyl, furyl, thienyl, thiazolyl and like groups.

Suitable groups $R_2$ include the amino and hydroxyl groups and hydroxyl group substituted by a $C_{1-12}$ hydrocarbon group which may be aliphatic, alicyclic, aromatic or araliphatic and may be substituted by one or more fluorine, chlorine, bromine or iodine atoms or amino, hydroxyl, or alkylated or acylated amino or hydroxyl groups such as $C_1$—$C_7$ alkoxyl, aryloxyl or aralkoxyl.

Preferred groups $R_2$ include the amino, hydroxy, methoxy, ethoxy, propyloxy, butyloxy, 2-chloroethoxy and like groups.

Suitable groups $R_6$ include the methyl, ethyl, propyl, butyl, benzyl, hexyl, cyclohexyl, β-substituted ethyl such as β-chloroethyl and β-hydroxyethyl and like groups.

The preferred group $R_5$ is the methyl group. The preferred groups $R_6$ are the methyl, butyl, benzyl, cyclohexyl and 2-hydroxyethyl groups.

Although only one general formula (formula (VI)) has been used to represent the compounds of the inventions it should be realised that the invention covers all tautomeric forms of the compounds and both isomeric forms that occur when $R_4$ is a methyl group, that is, such forms as shown by formulae (VIIa–VIIe) and any equivalent form are also included in the invention.

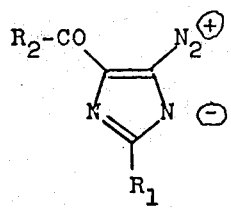

(VIIa)

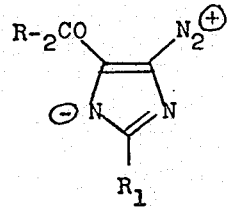

(VIIb)

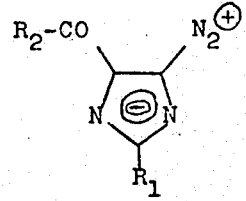

(VIIc)

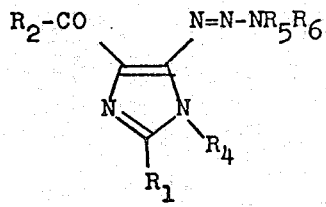

(VIId)

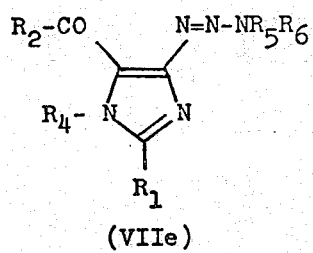

(VIIe)

In a second aspect the invention provides a process for the preparation of a compound of general formula (VI) which process comprises either or both of the steps in the following reacton scheme, and if required replacing or modifying groups $R_1$ and/or $R_2$ to form other groups $R_1$ and/or $R_2$ by methods known per se after the formation of the triazeno imidazole.

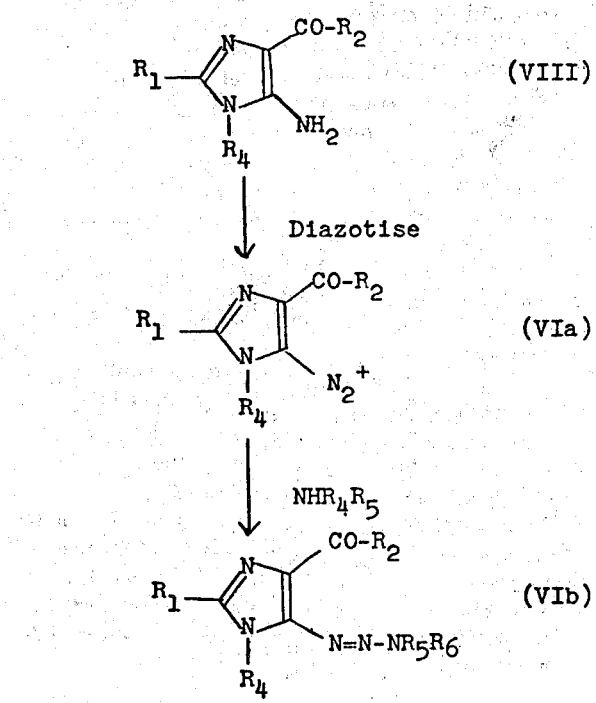

[In (VIa) when $R_4$ is a methyl group an external cation is present. Such ions include $Cl^-$, $Br^-$, $BF_4^-$ *and the like*]

The optional replacement or modification of groups $R_1$ and/or $R_2$ referred to above include known reactions such as the esterification of compounds in which $R_2$ is OH to provide compounds in which $R_2$ is, for example, an ethoxyl group; the production of compounds in which $R_2$ is OH by the removal of an esterifying group; or the formation of a compound in which $R_1$ is a hydroxyl substituted phenyl group by the removal of a protecting group such as a benzyl group by methods known per se.

The conversion of the amine (VIII) into diazonium salt (VIa) may be brought about by treating the amine (VIII) or an acid addition salt thereof, with nitrous acid or a nitrite salt or ester or the like in the presence of an acid capable of liberating nitrous acid from the said salt or ester.

The reaction will usually be carried out in water. Suitable nitrite salts include such salts as sodium and potassium nitrite, the sodium salt being preferred. Suitable acids include mineral acids such as sulphuric, nitric, hydrohalic, fluoroboric, phosphoric, and like acids or organic acids such as acetic formic or like acids. Hydrochloric acid is generally preferred.

This process is usually carried out in an aqueous medium using an excess of sodium nitrite with the slow addition of a mineral acid. The amine-imidazole (VIII) is preferably employed in the form of an acid addition salt, usually the hydrochloride.

One of the advantages of the compounds (VIb) is that they are more easily prepared than the corresponding 2-H compounds due to the stabilising effect of the aromatic group $R_1$ on the diazonium compound (VIa). Thus reaction temperatures need not be depressed (as in the preferred preparation of the corresponding 2-H compounds), although elevated temperatures should be avoided. We have found a temperature range of 0°–35°C suitable for the preparation of a compound (VIa), a room temperature reaction being particularly convenient.

The diazonium compounds of formula (VIa) are generally insoluble in water and are thus precipitated as they are formed. This allows isolation to be achieved simply by filtration. In those cases where the diazonium compound (VIa) are water soluble, they may be extracted with a suitable solvent such as chloroform and worked up in conventional manner. Purification, if desired, may be by recrystallization from an appropriate solvent such as cyclohexane or methanol.

An alternative method of carrying out this process that may be used when it is desirable to minimise possible side reactions is to add an acid solution of the amino-imidazole to one equivalent of an aqueous solution of a nitrite. This reaction will generally take place at a depressed or ambient temperature.

In cases where the diazonium compound is expected to be unstable it may be advantageous not to isolate it prior to further reaction but to carry out the next step of the reaction on the solution containing the crude diazonium compound.

When $R_4$ is a methyl group the diazonium compound is sufficiently unstable to require low temperatures, for example, 0°C, to be used during the reaction.

Compounds of general formula (VIa) which may be prepared by the diazitation processes described above include those of general formula (IX):

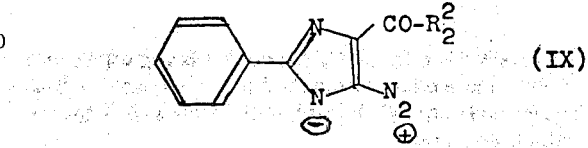

wherein $R_2^2$ is an OH or $NH_2$ group or a group $OR^3$ where $R^3$ is a methyl, ethyl, straight or branched chained propyl or butyl, hexyl, decyl, phenyl, benzyl, halo-substituted benzyl or ethyl, 2-diethylaminoethyl and cyclohexyl.

Compounds of general formula (VIa) which may be prepared by the diazotation processes described above include those of general formula (X):

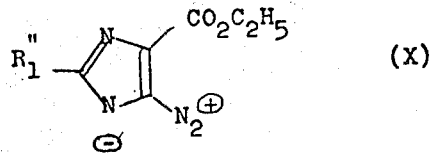

wherein $R_1$ is phenyl, monohalophenyl, hydroxyphenyl, dichlorophenyl, dibromophenyl, nitrophenyl, tolyl, trifluoromethylphenyl, $C_{1-6}$ alkoxyphenyl, dimethoxyphenyl, benzyloxyphenyl, phenylphenyl, carboethoxyphenyl, pyridyl, thienyl, furyl, thiazolyl, naphthyl and chloronaphthyl.

The conversion of the diazocompound (VIa) into the triazine compound (VIb) comprises reacting the compound (VIa) with an amine $HNR_5R_6$.

Generally an excess of the amine is used, the reaction taking place in a solvent medium such as an optionally aqueous alcohol such as methanol or ethanol or an ether solvent such as diethyl ether or tetrahydrofuran or a chlorinated hydrocarbon solvent such as chloroform.

The reaction may take place at low, ambient or elevated temperatures but low or ambient temperatures are usually preferred. Thus a suitable range is from 0°–180°C, particularly 0°–40°C. The products are generally solids which may be recrystallised from suitable solvents, such as methanol, ethyl acetate, or the like.

Compounds of general formula (VIb) which may be prepared by the general processes described herein include those of general formula (XI)

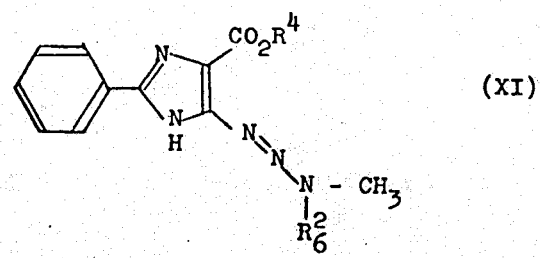

(XI)

wherein $R^4$ is $CH_3$ or $C_2H_5$ and $R_6^2$ is a methyl, ethyl, straight chained and branched propyl and butyl, hexyl, cyclohexyl, phenyl, benzyl, 2-dialkylaminoethyl or 2-haloethyl group.

Compounds of general formula (VIb) which may be prepared by the general process described herein also include those of general formula (XII):

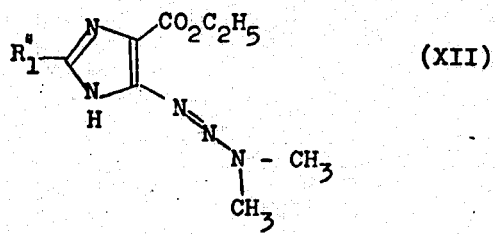

(XII)

wherein $R_1''$ is as previously defined.

The compounds of the invention of formula (VIb) show useful pharmacological activity, for example they have been shown to have bacteriacidal (see Example 57) and anti-fungal activity (see Example 58) and in particular have been shown to possess some anti-tumour activity in mice and dogs (see Examples 53 and 54), for example, activity is shown against the $R_1$ lymphoma and the ADJ/PC6 plasma-cell tumour.

Thus in a third aspect the invention provides a pharmaceutical composition useful at least for any of the aforesaid purposes which composition comprises a compound of formula (VIb) together with a pharmaceutically acceptable carrier. Suitable carriers include conventional binders, excipients, lubricants and other adjuvants for tablets, granules or capsules or sterile water for parenteral use.

The composition will usually be preferred in individual dosage units of between 5 mg. and 5g. and will generally by administered in an amount of from 0.5 to 250 mg/kg of body weight.

Although it is now thought that compounds of general formula (VIa) do not have sufficient biological activity for exploitation as medicinal compounds, they find utility as intermediates in the synthesis of the active compounds of general formula (VIb).

The starting amino imidazoles of general formula (VIII) may be prepared by the methods of Shaw et.al. (Journal of the Chemical Society, 1962 (2941), Cook et.al. (Journal of the Chemical Society, 1950, (1884)).

The method of synthesis comprises the reaction of an α-amino nitrile of formula

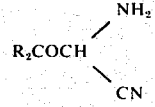

($R_2 \neq OH$)

with a benzylthioformamino hydrochloride of formula

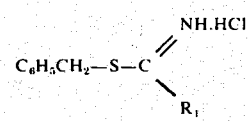

in an aprotic solvent preferably at an elevated temperature. Such a reaction is described in Example 59 herein.

Fuller details of the preparation of compounds of general formula (VIII) will be found in our German Offenlegungsschriften No. P2142831 and P2142832.

The following Examples serve to illustrate the invention.

In the Examples temperatures are given throughout in °C.

The structure of all compounds was checked by standard i.r. and n.m.r. techniques. All diazo compounds were seen to have a characteristic absorption band at about 2160 cm$^{-1}$, all triazines were seen to have a characteristic absorption band at about 1080 cm$^{-1}$. The methyl groups of all 3,3-dimethyltriazenes had a resonance integrating to 6 protons at about $\delta = 3.3$.

EXAMPLE 1.

4-Carbethoxy-5-diazo-2-phenylimidazole.

4-Amino-5-carbethoxy-2-phenylimidazole hydrochloride (37.0gm) was suspended in water (750 mls) containing sodium nitrite (15gm) and the mixture stirred at room temperature.

A solution of 2N hydrochloric acid (100 ml) was added in portions over five minutes and the mixture stirred 1 hour. The yellow product was collected, washed with water and dried in vacuo to give 31.4 gm of crude diazo compound.

Recrystallization from ethanol/water gave 26.3 gm of the pure 4-carbethoxy-5-diazo-2-phenyl imidazole mp 111°C (with decomposition). The product was soluble in organic solvents such as diethyl ether or chloroform and showed the characteristic diazo band in the infrared spectrum at about 2160 cm$^{-1}$.

Using the method of Example 1, the following compounds of Formula (VIa) were prepared ($R_4$ is a negative charge).

| Example. | $R_1$ | $R_2$ | mp°C (with decomposition) |
|---|---|---|---|
| 2 | $C_6H_4F(p)$ | $OC_2H_5$ | 122 |
| 3 | $C_6H_4NO_2(p)$ | " | >200 |
| 4 | 3-thienyl | " | 117 |
| 5 | 2-thienyl | " | 131 |
| 6 | 5-nitro-2-furyl | " | 183 |
| 7 | $C_6H_5$ | $OCH_2C_6H_4Cl(p)$ | 119 |
| 8 | $C_6H_5$ | $OCH_2C_6H_5$ | 126 |
| 9 | $C_6H_4F(o)$ | $OC_2H_5$ | 108 |
| 10 | $C_6H_5$ | $OCH_2CH_2CH_3$ | 88 |
| 11 | $C_6H_5$ | $OCH(CH_3)_2$ | 96 |
| 12 | $C_6H_5$ | $NH_2$ | 290 |

EXAMPLE 13.

4-Carbethoxy-5-(3,3-dimethyl1triazeno)-2-phenylimidazole.

A solution of 4-carbethoxy-5-diazo-2-phenylimidazole (8.0 gm) in methanol (75 ml) was treated with a 30% solution of dimethylamine in methanol (25 ml). The mixture was diluted with water to give the product as a pale yellow crystalline solid. This was collected, washed with water and dried in vacuo to yield 4-carbethoxy-5-(3,3-dimethyl-triazeno)-2-phenyl imidazole, 8.22g. A sample recrystallized from methanol/water yielded a pure product, mp 171°C.

EXAMPLE 14.

4-Carbethoxy-5-(3,3-dimethyltriazeno)-2-(p-fluorophenyl) imidazole.

4-Carbethoxy-5-amino-2-(p-fluorophenyl) imidazole hydrochloride (2.0g) was suspended in water (20 ml) containing sodium nitrite (1.0g). The mixture was stirred at room temperature and 1N hydrochloric acid (25 ml) added slowly. The mixture was stirred for 10 minutes and extracted with chloroform (25 ml). The phases were separated, the aqueous phase extracted with a further portion of chloroform (25 ml) and the combined chloroform solutions washed with saturated sodium chloride solution (25 ml). A solution of dimethylamine in ethanol (7 ml of a 25% solution) was added and the mixture evaporated to yield the crude product. This was recrystallized from ethanol/water to yield 4-carbethoxy-5-(3,3-dimethyltriazeno)-2-(p-fluorophenyl) imidazole, 1.55g, m.p. 177°C with decomposition.

EXAMPLES 15–41.

Compounds of the formula

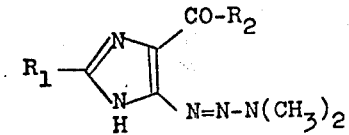

were prepared by the general methods analogous to those described in Examples 13 and 14.

| Example | $R_1$ | $R_2$ | mp°C (with decomposition) |
|---|---|---|---|
| 15 | $C_6H_4Cl(p)$ | $OC_2H_5$ | 144 |
| 16 | $C_6H_4CF_3(p)$ | " | 175 |
| 17 | $C_6H_4CH_3(p)$ | " | 177 |
| 18 | $C_6H_4NO_2(p)$ | $OC_2H_5$ | 176 |
| 19 | $C_6H_4OCH_3(p)$ | " | 168 |
| 20 | $C_6H_4OCH_2C_6H_5(p)$ | " | 168 |
| 21 | $C_6H_4—C_6H_5(p$ | " | 175 |
| 22 | $C_6H_4CH_3(m)$ | " | 176 |
| 23 | $C_6H_4F(m)$ | " | 177 |
| 24 | $C_6H_4F(o)$ | " | 130 |
| 25 | $C_6H_3(OCH_3)_2(3,4)$ | " | 180 |
| 26 | $C_6H_3Cl_2(3,4)$ | " | |
| 27 | $C_6H_3Cl_2(3,5)$ | " | 183 |
| 28 | 2-thienyl | " | 175 |
| 29 | 3-thienyl | " | 178 |
| 30 | 2-furyl | " | 148 |
| 31 | 4-thiazolyl | " | 171 |
| 32 | β-naphthyl | " | 194 |
| 33 | $C_6H_5$ | $OCH_3$ | 181 |
| 34 | " | $OCH_2CH_2CH_3$ | 167 |
| 35 | " | $OCH(CH_3)_2$ | 165 |
| 36 | " | $OCH_2C_6H_5$ | 88(Monohydrate) |
| 37 | " | $OCH_2C_6H_4Cl(p)$ | 155 |
| 38 | " | $OCH_2CH_2Cl$ | 166 |
| 39 | " | $NH_2$ | 178 |
| 40 | $C_6H_4Cl(p)$ | $NH_2$ | 170 (broad) |
| 41 | 2-thienyl | $NH_2$ | 193(broad) |

EXAMPLE 42.

4-Carbethoxy-5-(3-methyl-3-β-hydroxyethyl)triazeno-2-phenyl imidazole.

4-Carbethoxy-5-diazo-2-phenyl imidazole (4.84gm) in methanol (100 ml) was treated with a small excess of N-methyl ethanolamine. The mixture was diluted with petrol (60°–80°) until cloudy, and the product allowed to crystallize. 4-Carbethoxy-5-(3-methyl-3-β-hydroxyethyl)triazeno-2-phenyl imidazole was collected and recrystallized from ethyl acetate. The yield was 4.70 g. mp 158° with decomposition.

EXAMPLES 43–47.

Compounds of the formula

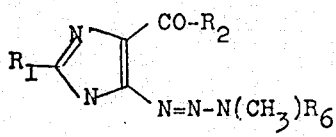

were prepared by methods analogous to that described in Example 42.

| Example | $R_1$ | $R_2$ | $R_6$ | mp (with decomposition) |
|---|---|---|---|---|
| 43 | $C_6H_5$ | $OC_2H_5$ | $C_6H_5$ | 167 |
| 44 | $C_6H_5$ | $OC_2H_5$ | $CH_2C_6H_5$ | 140 |
| 45 | $C_6H_5$ | $OC_2H_5$ | $CH_2CH_2CH_2CH_3$ | 118 |
| 46 | $C_6H_5$ | $OC_2H_5$ | cyclo $C_6H_{11}$ | 132 |
| 47 | $C_6H_4Cl(p)$ | $OC_2H_5$ | $CH_2C_6H_5$ | |

EXAMPLE 48.

4-Carbethoxy-5-(3,3-dimethyltriazeno)-2-(3-pyridyl) imidazole.

4-Carbethoxy-5-amino-2-(3-pyridyl)imidazole hydrochloride (1.90 gm) was dissolved in 5N hydrochloric acid (10 mls) and the mixture stirred at room temperature. A solution of sodium nitrite (0.5 gm) in water (5 ml) was then added in small portions, and the resulting clear solution stirred for 5 minutes. The mixture was then poured into a vigorously stirred mixture of 30% aqueous dimethylamine (1.0 ml) and 10% aqueous sodium carbonate (20 mls) giving a pale brown precipitate. The crude product was recrystallized from methanol/ether to give 0.65 gm of an off-white solid mp. 125° with decomposition.

EXAMPLE 49.

4-Carbethoxy-5-(3,3-dimethyltriazeno)-2-p-hydroxyphenyl imidazole.

A solution of 4-carbethoxy-5-(3,3-dimethyltriazeno)-2-p-benzyloxyphenyl imidazole (0.50 gm) in methanol(50 ml) was saturated with carbon dioxide, and 10% palladium on charcoal (100 mg) added. The mixture was hydrogenated at room temperature and pressure. Hydrogen (40 ml) was rapidly absorbed (4 minutes). The mixture was filtered and the filtrate evaporated to give a green residue. The product was dissolved in hot methanol, treated with charcoal, and recipitated by the addition of 60-80 petrol, as a light brown powder. mp 192° (with decomposition), yield 170 mgs. The NMR Spectrum confirmed the retention of the dimethyltriazeno function, while showing the complete removal of the benzyl protecting group.

EXAMPLE 50.

5-(3,3-Dimethyltriazeno)-2-phenylimidazole-4-carboxylic acid.

A solution of 4-carbobenzoxy-5-(3,3-dimethyltriazeno)-2-phenyl imidazole (1.0 gm) in methanol (50 ml) was saturated with carbon dioxide, and 10% palladium on charcoal (100 mgs) added. The mixture was hydrogenated at room temperature and pressure. A volume of 60 ml of hydrogen was absorbed in 1 hour 20 minutes.

The mixture was filtered and the filtrate evaporated to give a dark red oil, which was dried in vacuo over phosphorous pentoxide to yield 600 mgs. of red solid. The NMR spectrum showed complete removal of the benzyl group. mp indistinct, a slow decomposition was observed at about 140°C.

EXAMPLE 51.

Hydrochloride salt of 4-carbethoxy-5-(3,3-dimethyltriazeno)-2-phenyl imidazole.

4-Carbethoxy-5-(3,3-dimethyltriazeno)-2-phenyl imidazole (47.4 gm) was stirred in methanol (500 ml) at room temperature, and concentrated hydrochloric acid (20 ml) added, giving a clear solution. The well stirred mixture was diluted with anhydrous ether (4 liters) and the product slowly crystallized. It was collected, washed well with ether and dried in vacuo, to yield 52.0 gm of an off-white solid, mp. ca 125° with decomposition. It contained 1 molecule of water of crystallization.

EXAMPLE 52.

Monohydrate of 4-carbethoxy-5-(3,3-dimethyltriazeno)-2-phenyl imidazole.

4-Carbethoxy-5-(3,3-dimethyltriazeno)-2-phenyl imidazole (10.0 gm) was stirred at room temperataure in pH 7.0 phosphate buffer. The initial lemon-yellow colour slowly faded, and after 3 hours the mixture was almost colourless. The product was collected, washed with water and dried in vacuo over phosphorous pentoxide. The yield was 10.40 gm. The water was removed only very slowly by drying over phosphorous pentoxide.

The product was compared with the anhydrous material by infra-red spectra. The following characteristic peaks were observed in cm$^{-1}$

| (nujol mulls) | | (C=O) | | (Triazine) |
|---|---|---|---|---|
| anhydrous | — | 1710 | — | 1080 |
| monohydrate | 3250, | 1650, | 1130, | 1080 |

The melting points and NMR spectra were unaffected by monohydrate formation.

EXAMPLE 53.

Compounds of the invention have been shown to have antitumour properties against the R1 lymphoma in mice. The R1 lymphoma is normally sensitive to antimetabolites. Typically mice having a transplant of $1.5 \times 10^6$ tumour cells will die from the metastasizing tumour on day 9 to 11 after reansplant.

The compounds illustrated below were dosed by the intra peritoneal route in a vehicle of 10% acetone in arachas oil daily from day 3 to day 7 after tumour transplant. The increase in survival time over control was measured.

| Compound of Example No. | Dose mg./kg | Radian % increase in Survival time. |
|---|---|---|
| Control | — | 0 |
| 39 | 50 | 80 |
| 33 | 16 | 400 |
| 13 | 32 | 300 |
| 41 | 128 | 50 |
| 47 | 100 | 40 |
| 19 | 33 | 50 |
| 22 | 128 | 150 |
| 24 | 10 | 100 |
| 25 | 33 | 200 |
| 32 | 128 | 170 |
| 29 | 33 | 200 |
| 48 | 32 | 170 |
| Methotrexate (4-Amino-10-methyl-folid acid). | 2 | 100 |

EXAMAPLE 54

The breadth of antitumour spectrum of the compounds of the invention in mice is illustrated by their activity in the ADJ/PC6 plasma cell tumour. This is a solid tumour sensitive to most alkylating agents. Good activity is rarely seen against this tumour and the R1 lymphoma. The percentage inhibition of tumour weight is compared with controls and the therapeutic index shows the dose at which 90% inhibition occurs ($ID_{90}$) compared with the dose at which 50% of the animals were killed ($LD_{50}$).

| Compound of Example No. | Dose i.p. dosing × 5 $LD_{50}$ | $ID_{90}$ | Therapeutic Index. |
|---|---|---|---|
| 39 | 240mg/kg | 16.0mg/kg | 15 |
| 13 | 310mg/kg | 3.5mg/kg | 88 |
| 14 | 200mg/kg | 20mg/kg | 10 |
| Methotrexate | — | Inactive | — |

EXAMPLE 55.

Activity of these compounds has also been shown in Friend Leukaemia. Friend leukaemia virus is a prolonged infection in mice produced splenomegally. Compound of Example No. 13 dosed sub-cutaneously at 250 mg/kg/day on day −1, +1, +2 and +3 with respect to infection gave complete inhibition of the splenomegally.

EXAMPLE 56.

Certain of the compounds of the invention are less toxic than related previously known compounds. For example, the compound of Example No.13 and Dimethyltriazenoimidazole carboxamide (D.I.C.) have been given both by the oral and intravenous route to male and female mature beagle dogs. The dose regimen was 20mg/kg on day 0 45 mg on day 4 and a final dose of 90mg/kg given on day 9. The compound of Example No.13 dosed orally and intravenously showed no adverse clinical signs, the animals remaining in good health. D.I.C. administered by either route, showed a massive decrease in total circulating white cells and platelets. Oral dosing of D.I.C. with one dog had to be stopped after the second dose. None of these effects were noted with compound of Example No.13 at these dose levels.

EXAMPLE 57.

Compounds of this invention have shown antibacterial activity. Thus the minimum inhibitory concentration of compound of Example No.13 in DST agar + 5% lysed horse blood is illustrated against the following bacteria.

| Staphylococcus aurus | M.I.C. | 10µg/ml. |
|---|---|---|
| Steptococcus haemolyticus | M.I.C. | 1µg/ml. |

EXAMPLE 58.

Antifungal activity has been found in compounds of this invention. Thus compound of Example No. 13 has the following minimum inhibitory concentrations.

| Candida albicans | 10µg/ml |
|---|---|
| C. neoformans | 10 – 50µg/ml |
| Trychopyton mentagrophytes | 10µg/ml |

This activity against Candida and related organisms is especially useful in potentially anti-leukaemia agents as secondary micoses, especially due to such organisms, are becoming increasingly important as a contributory cause of death in leukaemia (see J. G. Gruhn, Cancer, 16, 61 (1963)

EXAMPLE 59.

5-Amino-4-carbethoxy-2-phenyl imidazole.

Phenylformamino benzyl thioether hydrochloride (29.0 gm) was refluxed in chloroform (200 ml) with ethyl aminocyanoacetate (170 gm) for 1 hour. On standing for eight hours the addition of dry diethyl ether (250 ml) caused the precipitation of the hydrochloride salt of 5-amino-4-carbethoxy-2-phenyl imidazole (25 g) m.p. 228°C after recrystallization from ethanol. (Treatment of the salt with aqueous sodium carbonate gave the free base).

EXAMPLE 60.

5-Carbethoxy-4-(3,3-dimethyltriazeno)-1-methyl-2-phenyl imidazole.

4-Amino-5-carbethoxy-1-methyl-2-phenyl imidazole (2.84 gm) (made by the method of Cook et al., Journal of the Chemical Society, 1950 (2775)) in 5N hydrochloric acid (24.0 ml) was cooled to 0°C and a cold solution of sodium nitrite (0.96 gm) in water (5 ml) added slowly, with stirring, keeping the mixture at 0°C. The resulting solution was added dropwise to a cold (0°C) mixture of sodium carbonate (120 mls of 30%) and dimethylamine (2.5 mls of 25% aqueous solution).

The product was separated as a gum, which was triturated with a mixture of petrol and diethyl ether to give a light brown solid. The yield was 1.7 gm, mp 79° with decomposition.

What we claim is:

1. A compound of the formula

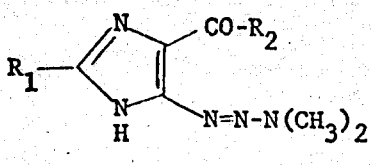

wherein
R₁ is phenyl; and
R₂ is methoxy, ethoxyl, n-propoxyl, or isopropoxyl, or a pharmaceutically acceptable, nontoxic acid addition salt or monohydrate thereof.

2. A compound according to claim 1 wherein R₂ is ethoxyl.

3. The compound according to claim 1 which is 4-carbethoxy-5-(3,3-dimethyl-triazeno)-2-phenyl-imidazole.

4. The compound according to claim 1 which is the hydrochloride salt of 4-carbethoxy-5-(3,3-dimethyl-triazeno)-2-phenyl imidazole.

5. The compound according to claim 1 which is the monohydrate of 4-carbethoxy-5-(3,3-dimethyl-triazeno)-2-phenyl imidazole.

* * * * *